United States Patent
Borzatta et al.

(10) Patent No.: US 9,247,750 B2
(45) Date of Patent: Feb. 2, 2016

(54) POLYENYLCYCLOPROPANECARBOXYLIC ESTERS WITH HIGH INSECTICIDAL ACTIVITY

(75) Inventors: Valerio Borzatta, Bologna (IT); Greta Varchi, Bologna (IT); Elisa Capparella, Ravenna (IT); Alberto Guerrini, Mezzano (IT); Arturo Battaglia, Imola (IT); Federico Trefiletti, Genoa (IT)

(73) Assignee: Endura S.P.A., Bologna (IT)

( * ) Notice: Subject to any disclaimer, the term of this patent is extended or adjusted under 35 U.S.C. 154(b) by 277 days.

(21) Appl. No.: 12/678,695

(22) PCT Filed: Sep. 15, 2008

(86) PCT No.: PCT/EP2008/062257
§ 371 (c)(1),
(2), (4) Date: Mar. 17, 2010

(87) PCT Pub. No.: WO2009/037228
PCT Pub. Date: Mar. 26, 2009

(65) Prior Publication Data
US 2010/0210721 A1    Aug. 19, 2010

(30) Foreign Application Priority Data
Sep. 17, 2007    (IT) .......................... MI2007A001790

(51) Int. Cl.
*A01N 53/00* (2006.01)
*C07C 67/343* (2006.01)
*C07C 69/743* (2006.01)

(52) U.S. Cl.
CPC .............. *A01N 53/00* (2013.01); *C07C 67/343* (2013.01); *C07C 69/743* (2013.01); *C07C 2101/02* (2013.01)

(58) Field of Classification Search
USPC ..................................... 514/531; 560/24, 124
See application file for complete search history.

(56) References Cited

FOREIGN PATENT DOCUMENTS

| DE | 21 13 124 | A1 | 11/1971 |
|---|---|---|---|
| DE | 22 31 436 | A1 | 1/1973 |
| DE | 38 18 761 | A1 | 12/1989 |
| EP | 0 939 073 | A | 9/1999 |

OTHER PUBLICATIONS

Ujihara, Kazuya et al. (DN 131:199442, HCAPLUS, Abstract of EP 939073).*
Mori, Tatsuya (DN 139:133688, HCAPLUS, abstract of JP 2003206264).*
Elliott, M. et al. 1976 "Insecticidal Activity of the Pyrethrins and Related Componds X. 5-Benzyl-3-Furylmethyl 2,2-Dimethylcyclopropanecarboxylates with Ethylenic Substituents at Position 3 on the Cyclopropane Ring" *Pesticide Science* 7(1):499-502.
Crombie, L. et al. 1970 "Syntheses of $^{14}$C-Labelled (+)-trans-Chrysanthemum Mono- and Dicarboxylic Acids, and of Related Compounds" *J Chem. Soc (C)* Part II: 1076-1080.
Dijkstra, P.J. et al. 1987 "Use of Pyrylium Synthons in the Synthesis of Hemispherands with Modified Cavitites. X-ray Structures of the 21-Hemispherands and a Pyrido Hemispherand" *J. Org. Chem.* 52:2433-2442.
Vedejs, E and Fang, W. 1984 "An *E*-Selective 1,3-Diene Synthesis from Moderated Ylides and Aldehydes" *J. Org. Chem.* 49:210-212.
Wakasugi, K. et al. 2003 "Simple, Mild, and Practical Esterification, Thioesterification, and Amide Formation utilizing *p*-Toluenesulfonyl Chloride and *N*-Methylimidazole" *Adv. Synth. Catal.* 345:1209-1214.
Wang, Y. and West, F.G. 2002 "A Convenient Method for the Synthesis of Terminal (E)-1,3-Dienes" *Synthesis* 1:99-103.

* cited by examiner

*Primary Examiner* — Sabiha N Qazi
(74) *Attorney, Agent, or Firm* — LeClairRyan, a Professional Corporation

(57) ABSTRACT

Described are new insecticide compounds that are derived from 2,2-dimethyl-3-(2-methylpropenyl)cyclopropanecarboxylic acid, also known as chrysanthemic acid, insecticidal compositions that contain the compounds, methods of synthesizing the compounds and methods of eliminating harmful insects from a substrate including bringing the substrate into contact with an effective amount of one or more such compounds.

12 Claims, 2 Drawing Sheets

Compound of example 1

Compound of example 2

Compound of example 3

Compound of example 4

Compound of example 8

Comparative compound of example 7

POLYENYLCYCLOPROPANECARBOXYLIC ESTERS WITH HIGH INSECTICIDAL ACTIVITY

RELATED APPLICATIONS

This application is a U.S. National Phase of International Application No.: PCT/EP2008/062257, filed Sep. 15, 2008, designating the U.S. and published in English on Mar. 26, 2009 as WO 2009/037228, which claims the benefit of Italian Application No. MI2007A001790, filed Sep. 17, 2007.

FIELD OF THE INVENTION

The present invention relates to the field of insecticides derived from chrysanthemic acid.

STATE OF THE ART 2,2-dimethyl-3-(2-methylpropenyl)cyclopropanecarboxylic acid (chrysanthemic acid) is a starting material for the synthesis of a number of pyrethroid insecticides, widely used in agriculture and the domestic field for controlling ants, spiders, mosquitoes, flies and other unwanted insects. The esters of said acid and their derivatives in position 3 of the cyclopropane ring are of particular interest. Included among them are the 3-dichlorovinyl derivative esterified with 2,3,5,6 tetrafluorobenzyl alcohol (transfluthrin), and (2,3,5,6-tetrafluoro-4-methoxy-methyl)benzyl-2,2-dimethyl-3-prop-1-enylcyclopropanecarboxylate (metofluthrin); metofluthrin and other similar compounds are described in EP-A-939 073. Other 3-vinyl-2,2,dimethylcyclopropanecarboxylic derivatives esterified with furyl or thienyl alcohols are known from DE-A-2 113 124. In EP-A-31 041 phenoxybenzyl esters of cyclopropanecarboxylic acid, containing in position 3 a mono/poly-halogenated diene substituent are described. *Pestic. Sci.*, 1976, 7, p. 499-502 describes 3-alkadienylcyclopropanecarboxylic derivatives, in which the carboxyl is esterified with 5-benzyl-3-furanmethanol. Similar derivatives are known from DE-A-2 231 436.

Despite the introduction of the different aforementioned insecticides, the need was however felt for new higher strength insecticidal compounds, with a wide spectrum of action and well tolerated by man and animals.

SUMMARY

Figure 1:
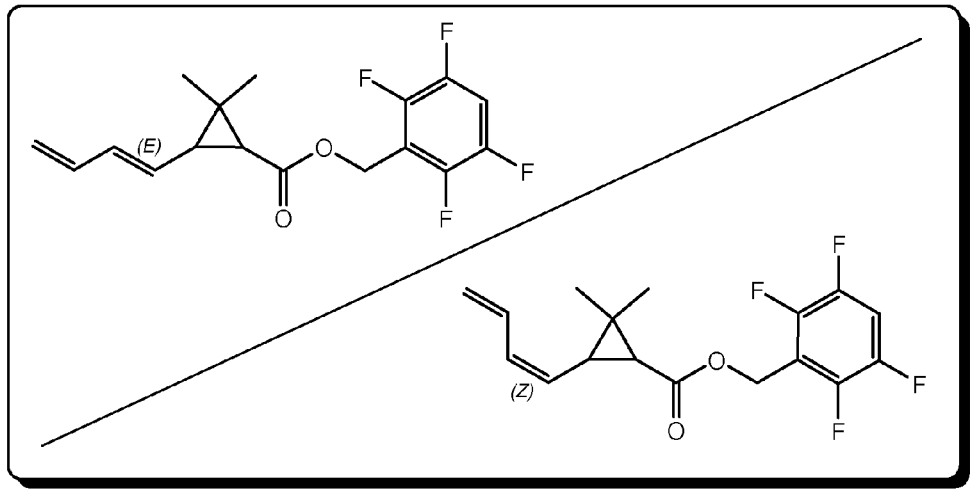
FIG. 1: Structure of the compounds of examples 1-3 of the invention with stereochemical indicators.
Figure 1:
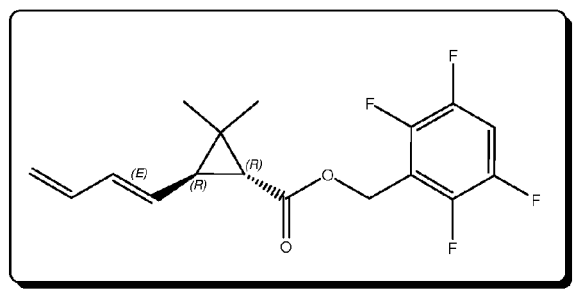
Figure 1:
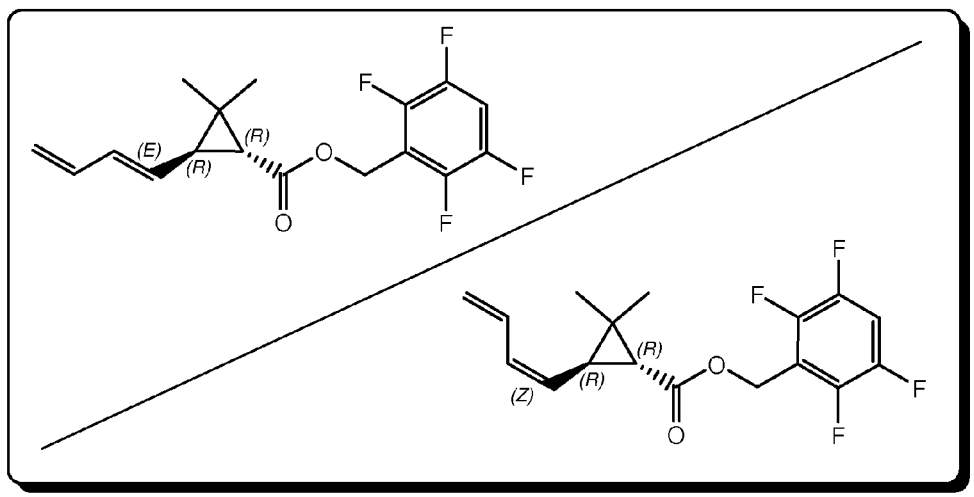
Figure 2:
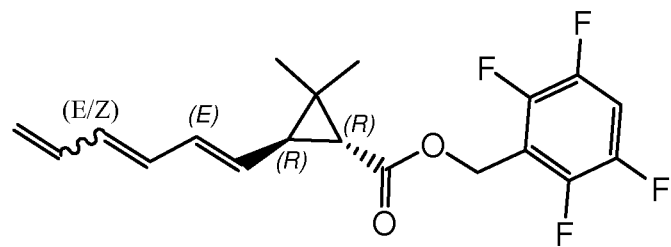
FIG. 2: Structure of the compounds of examples 4 and 8 of the invention and of comparative compound of example 7 with stereochemical indicators.
Figure 2:
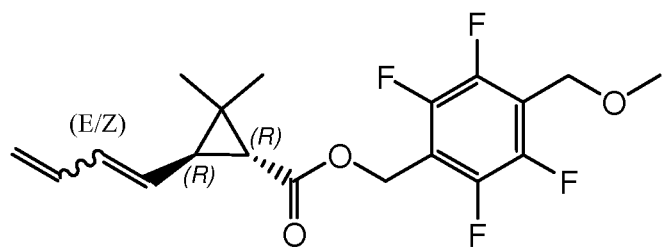
Figure 2:
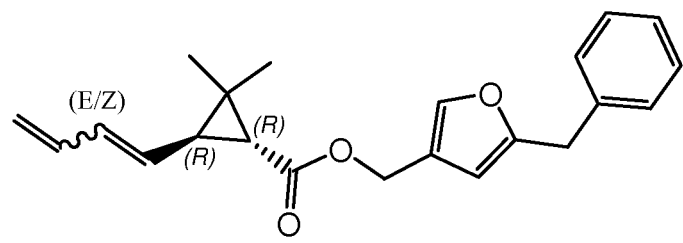

It has now been found that compounds of structural formula (I)

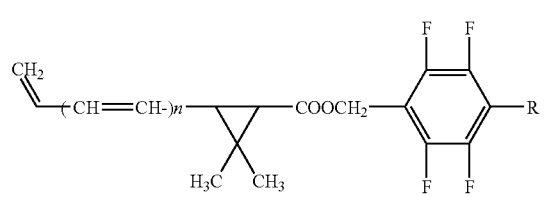

wherein n is chosen from 1 and 2 and R is chosen from —H, —$CH_3$, $C_2H_5$, —$OCH_3$, —$OC_2H_5$, and —$CH_2$—$OCH_3$ exhibit an unexpectedly high insecticidal activity.

DETAILED DESCRIPTION

The preferred compounds according to the invention are those having formula (I) wherein R is H or —$CH_2$—$OCH_3$. Particularly preferred are the following compounds:

2,3,5,6-tetrafluorobenzyl-(1RS,3RS)-3-((E/Z)-Buta-1,3-dienyl)-2,2-dimethylcyclopropane-1-carboxylate;

2,3,5,6-tetrafluorobenzyl-(1R,3R)-3-((E)-Buta-1,3-dienyl)-2,2-dimethylcyclopropane-1-carboxylate;

2,3,5,6-tetrafluorobenzyl-(1R,3R)-3-((E/Z)-Buta-1,3-dienyl)-2,2-dimethylcyclopropane-1-carboxylate;

2,3,5,6-tetrafluorobenzyl-(1R,3R)-3-(Hexa-1,3(E)-5(E/Z)-1,3,5-trienyl)-2,2-dimethylcyclopropane-1-carboxylate;

2,3,5,6-tetrafluoro-4-methoxymethyl benzyl(1R,3R)-3-((E/Z)-Buta-1,3-dienyl)-2,2-dimethylcyclopropane-1-carboxylate.

The compounds of formula (I), compared to other commonly used 2,3,5,6 tetrafluorobenzyl esters of 2,2-dimethylcyclopropanecarboxylic acid derivatives, such as transfluthrin and metofluthrin, are found to be surprisingly more active. The spectrum of action is wide-ranging and includes common flying and crawling insects; preferred among the flying insects is the mosquito; preferred among the crawling insects are arthropods, for example the Blattellidae.

The invention comprises a process for the synthesis of the aforesaid compounds of formula (I). They can be produced by esterification of an acid of formula (II) with an alcohol of formula (III) where, in said formulas, n and R have the aforesaid meanings.

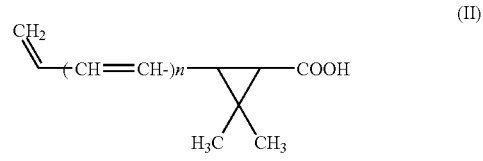

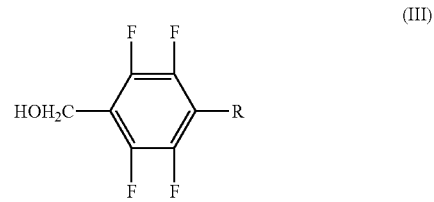

The esterification preferably takes place after activation of the COOH group of compound (II). Activation methods are known from the chemical literature, such as conversion of carboxyl to acyl halide; this latter is easily obtained for example by reacting compound (II) with an acyl chloride such as tosyl chloride, in the presence of a suitable amine such as N-methylimidazole, in acetonitrile as the solvent. The activated carboxyl, in the presence of alkaline catalysis, reacts at high yield with the alcohol (III) to provide the desired compound (I).

The precursor compounds of formula (III) are commercially available or can be produced by methods described in the literature.

The precursor compound of formula (IIa), (i.e. those of formula (II) with n=1) are obtainable on the basis of the following reaction scheme, where R' is a $C_1$-$C_3$ alkyl, preferably ethyl.

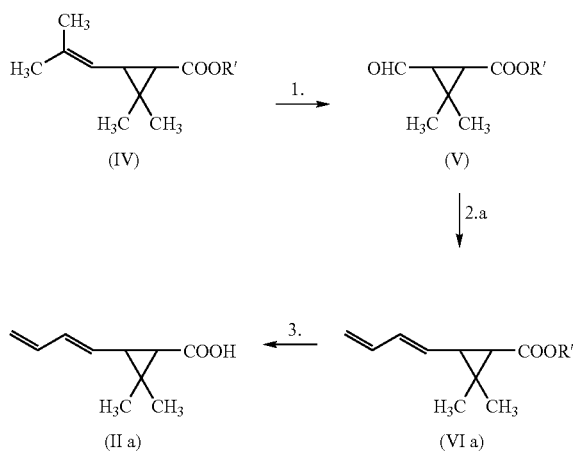

Step 1 is an ozonolysis reaction, achievable under conditions known from the chemical literature (P. J. Dijkstra et al. *JOC* 1987, 52, 2433-2442). Step 2.a is a Wittig reaction, carried out with an allyltriphenylphosphonium halide under conditions known to the skilled person of the art (cf. *J. Chem. Soc.* (C), 1970, p. 1076; Vedejs E. *JOC* 1984, 49, 210-212). The reaction can also be undertaken with diethyl allyl phosphonate (Wang J. et al. in *Synthesis* 2002, 99-103) (Horner Emmons reaction).

Step 3 is a hydrolysis with alkaline catalysis carried out under standard conditions. The compounds of formula (IIb) (i.e. those of formula (II) in which n=2) are obtainable on the basis of the following reaction scheme, where R' is a C1-C3 alkyl, preferably ethyl.

This scheme differs from the preceding in that at point 2.b two addition reactions are carried out: the first with a formylmethyltriphenylphosphonium halide (this reaction typically takes place in an aromatic solvent such as benzene, in the presence of triethylamine, at ambient temperature); the product obtained is then reacted with an allyltriphenylphosphonium halide, under the aforegiven conditions for this reagent.

The precursor compounds of formula (IV) (esters of chrysanthemic acid) are commercially available or can be produced by methods described in the literature as reported for example by Wakasugi et al. in *Adv. Synth. Catal.* 2003, 345, 1209-1214.

A particularly effective synthesis path for obtaining the compounds of formula (I) where n=2, with high yield and purity, comprises the formation of an aldehyde ester of formula (VII) where R has the meanings defined in formula (I).

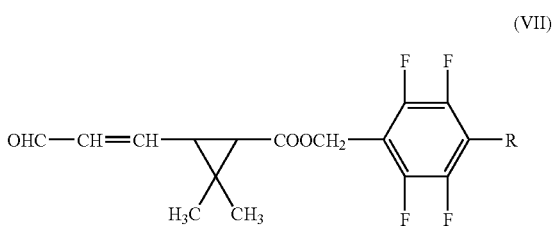

By converting the —CHO group of compound (VII) into an allyl group, the desired compounds of formula (I), with n=2, are obtained. The conversion into an allyl group is obtained by treating compound (VII) with an allyltriphenylphosphonium halide, under the aforestated conditions for this reagent.

The intermediates of formula (VII) are new, and as such constitute a further aspect of the invention. They can be themselves synthesized by treating a compound of formula (VIII) with a formylmethyltriphenylphosphonium halide, where R has the previously defined meanings.

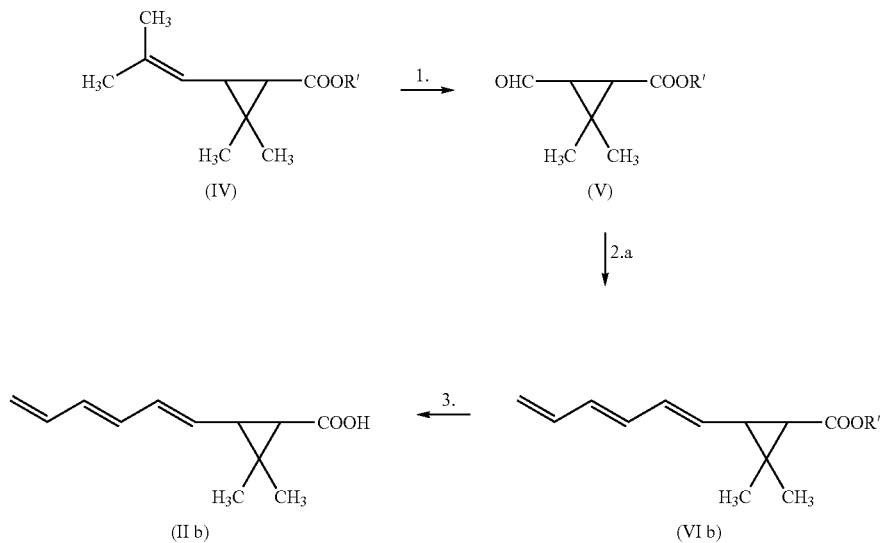

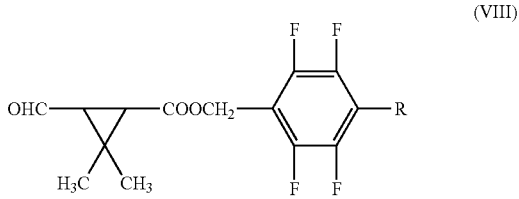

(VIII)

The reaction of compound (VIII) with the formylmethyltriphenylphosphonium halide takes place under the aforegiven conditions for this reagent.

The compound (VIII) can itself be obtained by ozonolysis starting from the corresponding ester of chrysanthemic acid having formula (IX).

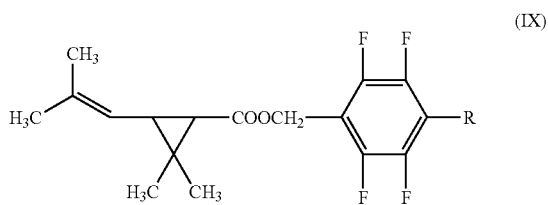

(IX)

The compound (IX) is easily obtained by esterification of chrysanthemic acid with the suitable 2,3,5,6 tetrafluorobenzyl alcohol (Wakasugi et al. in Adv. Synth. Catal. 2003, 345, 1209-1214).

The compounds of formula (I) of the invention are chiral, containing centres of asymmetry, and are optically active: they can be present in eight stereoisomeric forms for n=1 and in sixteen stereoisomeric forms for n=2 characterized by different geometric and optical isomery, and in their respective mixtures. The present invention therefore extends to the individual optical and geometric isomers having formula (I), and to mixtures thereof in any proportion.

The aforesaid optical and geometric isomers are obtained by applying the aforedescribed process on derivatives of formula (IV), (V), (VI a/b), (II a/b) having a specific optical and geometric configuration; said configuration is reproduced in the final compound (I). Specifically, to obtain the 1R,3R stereoisomer of compound (I), the corresponding 1R,3R stereoisomers of the intermediates (IV), (V), (VI a/b), (II a/b) are used. In order to obtain the 1S,3S stereoisomer of compound (I), the corresponding 1S,3S stereoisomers of the intermediates (IV), (V), (VI a/b), (II a/b) are used.

By working with enantiomeric mixtures (racemic or enantiomerically enriched) of the aforesaid precursor intermediates, the compounds of formula (I) are obtained in the corresponding mixtures.

Similarly, compounds of formula (I) with diastereoisomeric configuration (Z) or (E) are obtained starting from the intermediates (VI) and (II) having the same configuration, which are themselves obtainable from the aldehyde of formula (V) in a suitable configuration by Horner Emmons reaction with diethylallyl phosphonate.

The E/Z diastereoisomeric mixtures of the compounds of formula (I) are obtained starting from the corresponding diastereoisomeric mixtures of the aforestated precursor intermediates.

A further aspect of the present application is an insecticidal composition comprising one or more compounds of formula (I) as previously defined. Optionally, to complement and/or increase the spectrum of action, said compositions can contain, in addition to the compounds of formula (I), further insecticidal compounds chosen from those commonly available and more indicated for the chosen treatment. Synergistic compounds, i.e. not themselves insecticides but which contribute to increasing the activity of the compounds of formula (I), can be included in the compositions; synergistic compounds such as, e.g., piperonyl butoxide and 1-(3,4-dimethoxyphenyl)ethyl 2-butyn-1-yl ether, known as Verbutin, are well known in the insecticide field.

The insecticidal composition can be produced in solid form (e.g. powders, granules) or liquid form (solutions, suspensions, emulsions, microemulsions) using techniques known in the art. The formulation can also be encapsulated to achieve modulated release over time. In the present insecticidal compositions, the compound of formula (I) is contained in a weight/weight percentage comprised between 0.001% and 95%, preferably between 0.001% and 50%, and more preferably between 0.001% and 5%. If two or more compounds of formula (I) are used, the aforesaid weight percentages would refer to the overall sum of the compounds of formula (I) present in the composition. In addition to the is aforementioned active principles, adjuvants chosen from those commonly used in insecticidal compositions can be present. These include emulsifiers, UV stabilizers, antioxidants and other additives that are non-specific for insecticidal activity but useful for the specific application. Examples of emulsifiers are dodecylbenzenesulphonate, lignosulphonates, phospholipids, polyethylene glycols. Examples of UV stabilizers are 2-hydroxy-4-methoxybenzophenone, 2-hydroxy-4-octoxy-benzophenone, 4-hydroxy-2,2,6,6-tetramethylpiperidine sebecate. An example of an antioxidant is 2,6-di-tert-butyl-1-hydroxy-toluene. A further aspect of the present application is a process for preparing the aforesaid insecticidal compositions comprising mixing one or more compounds of formula (I) as previously defined with one or more excipients useful for insecticidal formulations, and optionally other active principles with insecticidal activity, and synergistic compounds.

The invention also includes a method for eliminating insects, characterized by bringing into contact a substrate containing said insects with one or more of the aforedefined suitably formulated compounds of formula (I); the substrate can be an enclosed environment (house, school, office and other public premises, etc) or an open environment (gardens, parks, surfaces of agricultural use, etc); the substrate can be an article, e.g. fabrics, mattresses, carpets containing the insects to be eliminated; the substrate can be the air present in one of said environments or one of the surfaces that comprise said environments; the substrate can also be the surface of an animal contaminated by insects; in this latter case the compounds of formula (I) can be applied directly onto the animal after suitably formulating with suitable excipients for veterinary use. The compound of formula (I) is dispensed at the times and in amounts determined on the basis of the volume of the environment to be treated, and the degree of its infestation. The compounds of formula (I) present a low toxicity to man and animals and can therefore be used with a wide safety margin.

The following non-limiting examples serve to illustrate the invention.

EXAMPLE 1

2,3,5,6-tetrafluorobenzyl-(1RS,3RS)-3-((E/Z)-Buta-1,3-dienyl)-2,2-dimethylcyclopropane-1-carboxylate a. Synthesis of (1RS,3RS)-3-((E/Z)-Buta-1,3-dienyl)-2,2-dimethylcyclopropane-1-carboxylic acid (1RS,3RS)-3-((E/Z)-Buta-1,3-dienyl)-2,2-dimethylcyclopropane-1-carboxylic acid is prepared from the corresponding ethyl(1RS,3RS)-3-carboxyaldehyde-2,2-dimethylcyclopropane-1-carboxylate, obtained by ozonolysis of racemic 80:20 trans/cis chrysanthemic acid ethyl ester; the ozonolysis product is then subjected to a Wittig reaction with allyl triphenylphosphonium bromide as described in *J. Chem. Soc.* (C),1076, (1970), followed by alkaline hydrolysis of the ester, after purification on silica gel column with 100/1 (v/v) petroleum ether/ethyl ether as eluent. The resulting acid, obtained by acidification of the corresponding salt, is used in the crude form for the subsequent reaction.

b. Synthesis of 2,3,5,6-tetrafluorobenzyl-(1RS,3RS)-3-((E/Z)-Buta-1,3-dienyl)-2,2-dimethylcyclopropane-1-carboxylate 3.4 ml (43 mmol) of N-methylimidazole, $CH_3CN$ (43 ml) and finally 2.38 g (14.3 mmol) of (1RS,3RS)-3-((E/Z)-Buta-1,3-dienyl)-2,2-dimethylcyclopropane-1-carboxylic acid are introduced into a flask under nitrogen atmosphere. The mixture is cooled to 0° C. and a solution of 3.26 g (17.2 mmol) of tosyl chloride dissolved in 19 ml of $CH_3CN$ is added. At the end of the addition, the mixture is left at ambient temperature for 45 minutes, then cooled again to 0° C. and 2.6 ml (14.3 mmol) of 2,3,5,6-tetrafluorobenzyl alcohol dissolved in 16 ml of $CH_3CN$ are added. The mixture is agitated at ambient temperature for 4 hours, diluted with $H_2O$ and transferred into a separating funnel. The reaction mixture is extracted 3 times with ethyl ether and the organic phases washed with water and with a saturated NaCl solution. The ether phase is separated, dried over $Na_2SO_4$ and filtered. Following evaporation at 21 mbar/30° C., the crude reaction product is taken up in 100/1 (v/v) petroleum ether/ethyl ether and purified on a silica gel chromatography column using the same eluent. By evaporation of the solvent, 4.61 g of an oily product with a purity equal to 97.0% is obtained.

IR ($CDCl_3$, $cm^{-1}$) 3200, 3086, 2925, 1725, 1178.

$^1$H NMR ($CDCl_3$) δ 7.13-7.04 (m, 1H, CHAr), 6.75-6.65 (m, 1H, CH═(Z)), 6.33-6.08 (m, 4 vinyl CH (E)+(Z)), 5.45-5.39 (m, 1H, vinyl CH (Z)), 5.26-5.10+4.99-4.97 (m, 8H, 2 vinyl-$CH_2$+2$CH_2$O (E)+(Z)), 2.36-2.32 (m, 1H, CH-cyclopropane (Z)), 2.10-2.07. (m, 1H, CH-cyclopropane (E)), 1.58 (d, 1H, J=7.5 Hz, CH-cyclopropane (Z)), 1.54 (d, 1H, J=5.2 Hz, CH-cyclopropane (E)), 1.28 (s, 3H, Me, (Z)), 1.26 (s, 3H, Me, (E)), 1.1 (s, 6H, 2Me, (Z)+(E)).

$^{13}$C NMR ($CDCl_3$) δ 171.16, 171.07, 147.12-146.84 (m, aromatic C—F), 146.56-146.37 (m, aromatic C—F), 144.65-144.37 (m, aromatic C—F), 144.07-143.84 (m, aromatic C—F), 136.44, 133.15, 132.23, 131.77, 130.95, 128.32, 118.16, 115.75, 115.37 (t, J=18 Hz, aromatic-C), 106.61 (t, J=22 Hz, aromatic-CH), 53.59, 36.62, 35.04, 34.03, 32.43, 29.81, 29.68, 22.0, 21.91, 20.26, 20.23

EXAMPLE 2

2,3,5,6-tetrafluorobenzyl-(1R,3R)-3-((E)-Buta-1,3-dienyl)-2,2-dimethylcyclopropane-1-carboxylate a. Synthesis of (1R,3R)-3-((E)-Buta-1,3-dienyl)-2,2-dimethylcyclopropane-1-carboxylic acid (1R,3R)-3-((E)-Buta-1,3-dienyl)-2,2-dimethylcyclopropane-1-carboxylic acid is prepared from the corresponding ethyl(1R,3R)-3-carboxyaldehyde-2,2-dimethylcyclopropane-1-carboxylate, obtained by ozonolysis of (1R,3R) chrysanthemic acid ethyl ester by reaction with diethylallyl phosphonate according to the following reaction scheme:

5.02 ml (28.8 mmol) of diethylallyl phosphonate are dissolved in 43 ml of anhydrous tetrahydrofuran in a flask under nitrogen atmosphere. The mixture is cooled to −78° C. and 18 ml of a solution of 1.6 M butyllithium in n-hexane are added slowly. The mixture is left under agitation at −78° C. for 1 hour, then 30 ml of hexamethylphosphotriamide are added followed by 3.5 g (20.6 mmol) of ethyl(1R,3R)-3-carboxyaldehyde-2,2-dimethylcyclopropane-1-carboxylate. The mixture is agitated for 12 hours at ambient temperature, then 45 ml of a saturated ammonium chloride solution are added. Extraction is then carried out three times with 50 ml of ethyl ether. After drying over anhydrous sodium sulphate, the solution is evaporated under vacuum (21 mbar/30° C.) and the crude product purified on silica gel column, with 95/5 (v/v) petroleum ether/ethyl ether as eluent, to obtain an oily product with an E/Z ratio of 97/3.

b. Synthesis of 2,3,5,6-tetrafluorobenzyl(1R,3R)-3-((E)-Buta-1,3-dienyl)-2,2-dimethylcyclopropane-1-carboxylate In a similar way to that described in example 1 part b., 2.38 g (14.3 mmol) of (1R,3R)-3-((E)-buta-1,3-dienyl)-2,2-dimethylcyclopropane-1-carboxylic acid are added with 3.4 ml (43 mmol) of N-methyl imidazole dissolved in 43 ml of $CH_3CN$, and reacted with 3.26 g (17.2 mmol) of tosyl chloride dissolved in 19 ml of $CH_3CN$ then with 2.6 ml (14.3 mmol) of 2,3,5,6-tetrafluorobenzyl alcohol dissolved in 16 ml of $CH_3CN$. After purification on silica gel column with 100/1 (v/v) petroleum ether/ethyl ether as eluent, 4.58 g of an oily product with an E/Z ratio of 97/3 and a purity equal to 96.1% are obtained.

IR ($CDCl_3$, $cm^{-1}$) 3201, 3085, 2930, 1725, 1176.

$^1$H NMR ($CDCl_3$) δ 7.15-7.07 (m, 1H, CHAr), 6.37-6.18 (m, 2H, 2CH═), 5.38-5.45 (m, 1H, vinyl CH), 5.28-5.20 (m, 2H, $CH_2$O), 5.18 (dd, $J_1$=2 Hz, $J_2$=12 Hz, $CH_2$═), 4.98 (dd, $J_1$=2 Hz, $J_2$=12 Hz, $CH_2$═), 2.16-2.07 (m, 1H, CH-cyclopropane), 1.58 (d, 1H, J=7.5 Hz, CH-cyclopropane), 1.36 (s, 3H, Me), 1.18 (s, 3H, Me).

$^{13}$C NMR ($CDCl_3$) δ 171.05, 147.11-146.36 (m, 2 Aromatic C—F), 144.6-143.88 (m, 2 Aromatic C—F), 136.44, 136.43, 133.15, 130.93, 115.72, 115.68 (t, J=18 Hz, Aromatic-C), 106.59 (t, J=22 Hz, Aromatic-CH), 53.55, 36.61, 34.02, 29.79, 21.89, 20.21.

EXAMPLE 3

2,3,5,6-tetrafluorobenzyl(1R,3R)-3-((E/Z)-Buta-1,3-dienyl)-2,2-dimethylcyclopropane-1-carboxylate a. Synthesis of (1R,3R)-3-((E/Z)-Buta-1,3-dienyl)-2,2-dimethylcyclopropane-1-carboxylic acid In a similar way to that described in example 1 part a., (1R,3R)-3-((E/Z)-Buta-1,3-dienyl)-2,2-dimethylcyclopropane-1-carboxylic acid is prepared from the corresponding ethyl(1R,3R)-3-carboxyaldehyde-2,2-dimethylcyclopropane-1-carboxylate, obtained by ozonolysis of (1R,3R) chrysanthemic acid methyl ester; the ozonolysis product is then subjected to a Wittig reaction with allyl triphenylphosphonium bromide as described in *J. Chem. Soc.* (C),1076, (1970), followed by alkaline hydrolysis of the ester, after purification on silica gel column with 100/1 (v/v) petroleum ether/ethyl ether as eluent. The resulting acid, obtained by acidification of the corresponding salt, is used in the crude form for the subsequent reaction.

b. Synthesis of 2,3,5,6-tetrafluorobenzyl(1R,3R)-3-((E/Z)-Buta-1,3-dienyl)-2,2-dimethylcyclopropane-1-carboxylate In a similar way to that described in example 1 part b., 2.38 g (14.3 mmol) of (1R,3R)-3-((E/Z)-Buta-1,3-dienyl)-2,2-dimethylcyclopropane-1-carboxylic acid are added with 3.4 ml (43 mmol) of N-methyl imidazole dissolved in 43 ml of $CH_3CN$, and reacted with 3.26 g (17.2 mmol) of tosyl chloride dissolved in 19 ml of $CH_3CN$, then with 2.6 ml (14.3 mmol) of 2,3,5,6-tetrafluorobenzyl alcohol dissolved in 16 ml of $CH_3CN$. After purification on silica gel column with 100/1 (v/v) petroleum ether/ethyl ether as eluent, 4.64 g of an oily product with a purity equal to 94% are obtained.

IR ($CDCl_3$, $cm^{-1}$) 3200, 3086, 2925, 1725, 1178.

$^1H$ NMR ($CDCl_3$) δ 7.13-7.04 (m, 1H, CHAr), 6.80-6.65 (m, 1H, CH=(Z)), 6.33-6.08 (m, 4 vinyl CH (E)+(Z)), 5.45-5.39 (m, 1H, vinyl CH (Z)), 5.26-5.10+4.99-4.97 (m, 8H, 2 vinyl-$CH_2$+2$CH_2$O (E)+(Z)), 2.36-2.32 (m, 1H, CH-cyclopropane (Z)), 2.10-2.07. (m, 1H, CH-cyclopropane (E)), 1.58 (d, 1H, J=7.5 Hz, CH-cyclopropane (Z)), 1.54 (d, 1H, J=5.2 Hz, CH-cyclopropane (E)), 1.28 (s, 3H, Me, (Z)), 1.26 (s, 3H, Me, (E)), 1.1 (s, 6H, 2Me, (Z)+(E)).

$^{13}C$ NMR ($CDCl_3$) δ 171.16, 171.07, 147.12-146.84 (m, Aromatic C—F), 146.56-146.37 (m, Aromatic C—F), 144.65-144.37 (m, Aromatic C—F), 144.07-143.84 (m, Aromatic C—F), 136.44, 133.15, 132.23, 131.77, 130.95, 128.32, 118.16, 115.75, 115.37 (t, J=18 Hz, Aromatic-C), 106.61 (t, J=22 Hz, Aromatic-CH), 53.59, 36.62, 35.04, 34.03, 32.43, 29.81, 29.68, 22.0, 21.91, 20.26, 20.23.

EXAMPLE 4

2,3,5,6-tetrafluorobenzyl(1R,3R)-3-(Hexa-1,3(E)-5(E/Z)-trienyl)-2,2-dimethylcyclopropane-1-carboxylate The compound is prepared from (1R,3R)-3-carboxyaldehyde-2,2-dimethylcyclopropane-1-carboxylate of 2,3,5,6 tetrafluorobenzyl alcohol, obtained by ozonolysis of the corresponding chrysanthemic acid ester. Then 30.4 g (100 mmol) of aldehyde are reacted under nitrogen atmosphere with 40.9 g (120 mmol) of formylmethyltriphenyl phosphonium chloride in 500 ml of benzene in the presence of 15.15 g (150 mmol) of triethylamine at ambient temperature for 28 hours. The crude (1R,3R)-3-(3(E)-oxopropenyl)-2,2-dimethylcyclopropane-1-carboxylate of 2,3,5,6 tetrafluorobenzyl alcohol thus obtained, is purified after evaporation of the solvent at 25° C./21 mbar on silica gel chromatography column with 2/1 (v/v) petroleum ether/ethyl acetate as eluent, to obtain 26.7 g of product.

$^1H$ NMR ($CDCl_3$) δ 9.40 (d, 1H, J=8 Hz, CHO), 7.11-7.03 (m, 1H, CHAr), 6.49-6.42 (m, 1H, vinyl-CH), 6.24-6.17 (m, 1H, vinyl CH), 5.24-5.16 (m, 2H, $CH_2$O), 2.25 (q, 1H, J=4.8 Hz, CH), 1.86 (d, 1H, J=5.6 Hz, CH), 1.27 (s, 3H, Me), 1.22 (s, 3H, Me).

$^{13}C$ NMR ($CDCl_3$) δ 192.5, 169.8, 154.9, 147.1-146.3 (m, Aromatic C—F), 144.6-143.8 (m, Aromatic C—F), 134.0, 114.9 (t, J=16.6 Hz, Aromatic-C), 106.8 (t, J=22 Hz, Aromatic-CH), 60.2, 53.9, 36.0, 35.8, 31.5, 21.9, 20.2, 14.1.

The product obtained is added slowly at 0° C. to an ether solution (ethyl ether) of 45.7 g (118 mmol) of allyltriphenylphosphonium bromide in 300 ml of anhydrous ethyl ether, pre-cooled to 0° C., to which are added 11.1 ml of 1.6 M butyllithium solution in n-hexane. At the end of the addition the mixture is left for 1 hour at 0° C. then for 3 hours at ambient temperature. The solution is then filtered and concentrated at 20° C./21 mbar, to obtain an oil which is purified on silica gel column with 100/1 petroleum ether/ethyl ether as eluent. 27.2 g of an oily product with 96% purity are obtained.

IR ($CDCl_3$, $cm^{-1}$) 3203, 3083, 2919, 2530, 1721, 1172.

$^1H$ NMR ($CDCl_3$) δ 7.11-7.07 (m, 1H, CHAr), 6.34-6.16 (m, 4H, vinyl CH), 5.49-5.41 (m, 1H, vinyl CH), 5.23-5.05 (m, 4H, 2 vinyl-$CH_2$+2$CH_2$O), 2.13-2.01 (m, 1H, CH-cyclopropane), 1.63-1.56 (m, 1H, CH-cyclopropane), 1.27 (s, 3H, Me), 1.12 (s, 3H, Me).

$^{13}C$ NMR ($CDCl_3$) δ 171.88, 171.08, 137.0, 136.93, 132.8, 132.6, 132.4, 131.9, 131.7, 131.3, 129.6, 129.2, 117.0, 116.8, 106.6 (t, J=22 Hz, Aromatic-CH), 64.3, 38.3, 38.1, 34.8, 33.5, 29.7, 28.8, 21.9, 21.4.

EXAMPLE 5

Effectiveness of Insecticide in the Vapour Phase Against Mosquitoes of the Species *Aedes aegypti* and *Culex quinquefasciatus*

Test units consisting of a paper support 20 cm×10 cm in size were impregnated with the compound of example 3 and, for comparative purposes, with the reference compounds transfluthrin and metofluthrin, at an amount of 5.00 mg/unit for each compound (pure).

Using a common laboratory stand, the test unit was placed at a height of about 30 cm from the ground along one side of a 20 $m^3$ room (L 3.00 m×D 2.49 m×H 2.69 m). In order to homogenize the insecticidal air within the room, a small electric fan was placed on the floor diagonal to the surface of the unit, in the is nearest corner at a distance of about 50 cm from the unit. Three metal cages (L 8.4 cm×Ø 8.0 cm×mesh 1.0 mm) for every mosquito species, each containing 20 3-4 day old individuals of mixed sex, were placed along the other three sides of the room, at a height of 1.80 m from the ground and at a distance of 0.45 m from the respective walls. During the test the room was kept closed and temperature and humidity were controlled (T 23-26° C., RH 49-61%).

The fan was switched on and left on for 8 continuous hours. The times needed to reach 10%, 50% and 90% insect knockdown (KT10, KT50 and KT90, respectively) were recorded.

Every 2 hours and up to the 6$^{th}$ hour after the fan was switched on, new cages were introduced containing insects (set of 3 cages for each species).

At the end of the 8$^{th}$ hour, the percentage of insects knocked down in all the cages was determined, then the insects were removed from the room and transferred into an uncontaminated atmosphere within closed containers containing a sugary solution. The percentage mortality was recorded at the 24$^{th}$ hour from the start of the test.

The results obtained are summarized in tables 1 and 2 and the data are averages for the 3 cages.

TABLE 1

Tested species: *Aedes aegypti*

| Compound | Insect exposure after the following hours | Knock-down time (minutes) KT10 | KT50 | KT90 | % knock-down 8 h | % mortality 24 h |
|---|---|---|---|---|---|---|
| Example 3 | 0 | 16 | 19 | 25 | 100 | 100 |
| 5 mg/unit | 2 | 4 | 6 | 9 | 100 | 100 |
|  | 4 | 4 | 6 | 11 | 100 | 100 |
| Transfluthrin | 0 | 21 | 26 | 36 | 100 | 100 |
| 5 mg/unit | 2 | 5 | 9 | 12 | 100 | 100 |
|  | 4 | 4 | 7 | 10 | 100 | 100 |
| Metofluthrin | 0 | 23 | 30 | 39 | 100 | 100 |
| 5 mg/unit | 2 | 7 | 9 | 15 | 100 | 100 |
|  | 4 | 6 | 8 | 14 | 100 | 100 |

TABLE 2

Tested species: *Culex quinquefasciatus*

| Compound | Insect exposure after the following hours | Knock-down time (minutes) KT10 | KT50 | KT90 | % knock-down 8 h | % mortality 24 h |
|---|---|---|---|---|---|---|
| Example 3 | 0 | 20 | 23 | 31 | 100 | 100 |
| 5 mg/unit | 2 | 6 | 8 | 12 | 100 | 100 |
|  | 4 | 6 | 10 | 18 | 100 | 100 |
| Transfluthrin | 0 | 27 | 37 | 44 | 100 | 100 |
| 5 mg/unit | 2 | 7 | 14 | 20 | 100 | 100 |
|  | 4 | 9 | 17 | 22 | 100 | 100 |
| Metofluthrin | 0 | 26 | 30 | 35 | 100 | 100 |
| 5 mg/unit | 2 | 11 | 16 | 24 | 100 | 100 |
|  | 4 | 11 | 16 | 20 | 100 | 100 |

EXAMPLE 6

Effectiveness of Residual Insecticide on Surfaces Against Cockroaches of the Species *Blattella germanica*

Solutions of the compound of example 3 in acetone and, for comparison, of the reference compounds Transfluthrin and Metofluthrin were applied from a distance of 12 cm onto glazed tiles (Ostara model, 15×15 cm=225 $cm^2$) by means of a suitable glass sprayer, so as to obtain an applied amount of pure compound equal to 50 $mg/m^2$. After treatment the tiles were transferred to and maintained in a closed test room at controlled temperature and humidity (24-25° C., RH 50-60%). Glass rings (H 5.5 cm×Ø 9.5 cm), with their internal surface treated with talc, and each containing 5 cockroaches, were positioned at the centre of the tiles for each of the assessment times of 24 hours, 3, 7, 10 and 14 days following treatment. For each assessment day, the insects were maintained on the surface for 24 hours and the time (hours, minutes) necessary to attain 100% knock-down followed by death, or percentage knock-down at the end of 24 hours, were recorded. The results obtained are summarized in table 3:

TABLE 3

Tested species: *Blattella germanica*

| Compound | Amount applied ($mg/m^2$) | Time (hours, minutes) to reach 100% knock-down followed by death, or percentage knock-down after 24 hours | | | | |
|---|---|---|---|---|---|---|
|  |  | 1 day | 3 days | 7 days | 10 days | 14 days |
| EXAMPLE 3 | 50 | 15' | 15' | 15' | 15' | 15' |
| TRANSFLUTHRIN | 50 | 24 h 60% | 24 h 0% | 24 h 0% | — | — |
| METOFLUTHRIN | 50 | 2 h (24 h 80%*) | 24 h 40% | 24 h 0% | 24 h 0% | — |
| UNTREATED CONTROL | — | 24 h 0% | 24 h 0% | 24 h 0% | 24 h 0% | 24 h 0% |

*)one of the 5 individuals recovered within 24 hours from initial exposure.

The activity data presented in tables 1-3 show, for the compound of example 3 in accordance with formula (I) of the invention, a marked reduction in knock-down time for the different species tested. In particular, a very obvious increase in activity compared with the reference insecticides is observed with *Blattella germanica* (arthropod). In this respect, table 3 shows a total knock-down (100%) within 15 minutes of exposure for the compound of the invention; vice-versa, the reference insecticides, transfluthrin and metofluthrin, achieved only a partial knock-down i.e. between 60 and 80%, at 24 hours after exposure. The compounds of the invention hence demonstrate a decidedly superior strength; the diversity of the species on which activity is found also confirms the wide spectrum of action.

EXAMPLE 7

(2-benzyl-4-hydroxymethylfuryl) (1R,3R)-3-((E/Z)-Buta-1,3-dienyl)-2,2-dimethylcyclopropane-1-carboxylate (Comparative)

a. Synthesis of (1R,3R)-3-((E/Z)-Buta-1,3-dienyl)-2,2-dimethylcyclopropane-1-carboxylic acid In a similar way to that described in example 1 part a., (1R,3R)-3-((E/Z)-Buta-1,3-dienyl)-2,2-dimethylcyclopropane-1-carboxylic acid is prepared from the corresponding ethyl(1R,3R)-3-carboxyaldehyde-2,2-dimethylcyclopropane-1-carboxylate, obtained by ozonolysis of (1R,3R) chrysanthemic acid methyl ester; the ozonolysis product is then subjected to a Wittig reaction with allyl triphenylphosphonium bromide as described in *J. Chem. Soc.* (C),1076, (1970), followed by alkaline hydrolysis of the ester, after purification on silica gel column with 100/1 (v/v) petroleum ether/ethyl ether as eluent. The resulting acid, obtained by acidification of the corresponding salt, is used in the crude form for the subsequent reaction.

b. Synthesis of (2-benzyl-4-hydroxymethylfuryl) (1R,3R)-3-((E/Z)-Buta-1,3-dienyl)-2,2-dimethylcyclopropane-1-carboxylate In a similar way to that described in example 1 part b., 4.76 g (28.6 mmol) of (1R,3R)-3-((E/Z)-Buta-1,3-dienyl)-2,2-dimethylcyclopropane-1-carboxylic acid are added with 6.8 ml (86 mmol) of N-methyl imidazole dissolved in 86 ml of $CH_3CN$, and reacted with 6.52 g (34.4 mmol) of tosyl chloride dissolved in 38 ml of $CH_3CN$, then with 5.38 g (28.6 mmol) of 2-benzyl-4-hydroxymethyl-furan dissolved in 32 ml of $CH_3CN$. After purification on silica gel column with 100/1 (v/v) petroleum ether/ethyl ether as eluent, 9.1 g of an oily product with a purity equal to 96% are obtained.

IR ($CDCl_3$, $cm^{-1}$) 3200, 3086, 2925, 1725, 1178.
$^1$H NMR ($CDCl_3$ 400 MHz) δ 7.39-7.20 (m, 12H, (E+Z), Arom-CH+CH=(furan)) 6.80-6.68 (m, 1H, CH=; Z), 6.39-6.05 (m, 4H (E+Z),4CH=), 6.02 (s, 1H, CH=(furan); E), 5.50-5.40 (m, 1H, CH=; E), 5.30-5.05 (m, 4H (E+Z), CH=), 5.02-4.81 (m, 5H, (E+Z), 2$CH_2$+CH=), 3.95 (s, 2H, $CH_2$ (E)); 2.38-2.32 (m, 1H (Z), CH cyclopropane); 2.11-2.03 (m, 1H (E), CH cyclopropane); 1.60 (d, 1H (E), J=7.1 Hz, CH), 1.58 (d, 1H (Z), J=7.2 Hz, CH), 1.31 (s, 3H (Z), $CH_3$) 1.29 (s, 3H (E), $CH_3$), 1.19 (s, 6H (E+Z) $CH_3$).
$^{13}$C NMR ($CDCl_3$, 100 MHz) δ (E+Z) 171.74, 171.67, 155.58, 140.35, 137.70, 136.52, 132.35, 131.52, 131.34, 128.72, 128.51, 126.57, 121.21, 117.00, 115.57, 107.27, 77.21, 65.83, 57.97, 57.94, 36.28, 35.43, 34.53, 34.42, 34.10, 32.09, 29.45, 29.33, 22.60, 22.32, 22.10, 22.01, 20.32, 20.28, 15.26, 14.04.

EXAMPLE 8

2,3,5,6-tetrafluoro-4-methoxymethyl benzyl(1R,3R)-3-((E/Z)-Buta-1,3-dienyl)-2,2-dimethylcyclopropane-1-carboxylate a. Synthesis of (1R,3R)-3-((E/Z)-Buta-1,3-dienyl)-2,2-dimethylcyclopropane-1-carboxylic acid In a similar way to that described in example 1 part a., (1R,3R)-3-((E/Z)-Buta-1,3-dienyl)-2,2-dimethylcyclopropane-1-carboxylic acid is prepared from the corresponding ethyl(1R,3R)-3-carboxyaldehyde-2,2-dimethylcyclopropane-1-carboxylate, obtained by ozonolysis of (1R,3R) chrysanthemic acid methyl ester; the ozonolysis product is then subjected to a Wittig reaction with allyl triphenylphosphonium bromide as described in *J. Chem. Soc.* (C),1076, (1970), followed by alkaline hydrolysis of the ester, after purification on silica gel column with 100/1 (v/v) petroleum ether/ethyl ether as eluent. The resulting acid, obtained by acidification of the corresponding salt, is used in the crude form for the subsequent reaction.

b. Synthesis of 2,3,5,6-tetrafluoro-4-methoxymethyl benzyl(1R,3R)-3-((E/Z)-Buta-1,3-dienyl)-2,2-dimethylcyclopropane-1-carboxylate In a similar way to that described in example 1 part b., 4.76 g (28.6 mmol) of (1R,3R)-3-((E/Z)-Buta-1,3-dienyl)-2,2-dimethylcyclopropane-1-carboxylic acid are added with 6.8 ml (86 mmol) of N-methyl imidazole dissolved in 86 ml of $CH_3CN$, and reacted with 6.52 g (34.4 mmol) of tosyl chloride dissolved in 38 ml of $CH_3CN$, then with 6.41 g (28.6 mmol) of 2,3,5,6-tetrafluoro-4-methoxymethyl benzyl alcohol dissolved in 32 ml of $CH_3CN$. After purification on silica gel column with 100/1 (v/v) petroleum ether/ethyl ether as eluent, 9.5 g of an oily product with a purity equal to 96% are obtained.

IR ($CDCl_3$, $cm^{-1}$) 3200, 3095, 2932, 1732, 1178.
$^1$H NMR ($CDCl_3$ 400 MHz) δ 6.78-6.63 (m, 1H, CH=) 6.38-6.16 (m, 3H, CH=; Z+E), 5.38-5.46 (m, 1H CH=, E), 4.95-5.25 (m, 9H, 5CH=+2CH=; E+Z), 4.58 (m, 4H, (E+Z), 2$CH_2$), 3.41 (s, 6H (E+Z), $OCH_3$), 2.38-2.31 (m, 1H (Z), CH cyclopropane), 2.15-2.05 (m, 1H (E) CH cyclopropane); 1.58 (d, 1H (E), J=7.3 Hz, CH); 1.55 (d, 1H (Z), J=7.2 Hz, CH); 1.50 (s, 3H (Z), $CH_3$), 1.47 (s, 3H (Z), $CH_3$), 1.18 (s, 6H, 2$CH_3$).
$^{13}$C NMR ($CDCl_3$, 100 MHz) δ (E+Z) 171.10, 171.02, 146.45, 146.39, 146.31, 146.27, 146.23, 146.17, 143.99, 143.93, 143.87, 143.79, 143.75, 143.69, 136.42, 133.14, 132.22, 131.74, 130.92, 128.30, 118.12, 117.01, 116.83, 116.66, 115.71, 114.99, 114.82, 114.65, 65.78, 61.35, 59.43, 53.48, 36.60, 35.02, 34.02, 32.40, 9.77, 29.65, 21.97, 21.88, 20.25, 20.22, 15.21.

EXAMPLE 9

Effectiveness of Insecticide in the Vapour Phase Against Mosquitoes of the Species *Aedes aegypti* and *Culex quinquefasciatus*

Test units consisting of a paper support 20 cm×10 cm in size were impregnated with the compound of examples 3, 7 and 8 and, for comparative purposes, with the reference compounds transfluthrin and metofluthrin, at an amount of 5.00 mg/unit for each compound (pure). Using a common laboratory stand, the test unit was placed at a height of about 30 cm from the ground along one side of a 20 $m^3$ room (L 3.00 m×D 2.49 m×H 2.69 m). In order to homogenize the insecticidal air within the room, a small electric fan was placed on the floor diagonal to the surface of the unit, in the nearest corner at a distance of about 50 cm from the unit. Three metal cages (L 8.4 cm×Ø 8.0 cm×mesh 1.0 mm) for every mosquito species, each containing 20 3-4 day old individuals of mixed sex, were placed along the other three sides of the room, at a height of 1.80 m from the ground and at a distance of 0.45 m from the respective walls. During the test the room was kept closed and temperature and humidity were controlled (T 23-26° C., RH 49-61%). The fan was switched on and left on for 8 continuous hours. The times needed to reach 10%, 50% and 90% insect knock-down (KT10, KT50 and KT90, respectively) were recorded.

Every 2 hours and up to the $6^{th}$ hour after the fan was switched on, new cages were introduced containing insects (set of 3 cages for each species).

At the end of the $8^{th}$ hour, the percentage of insects knocked down in all the cages was determined, then the insects were removed from the room and transferred into an uncontaminated atmosphere within closed containers containing a sugary solution. The percentage mortality was recorded at the $24^{th}$ hour from the start of the test.

The results obtained are summarized in tables 1 and 2 and the data are averages for the 3 cages.

TABLE 1

Tested species: *Aedes aegypti*

| Compound | Insect exposure after the following hours | Knock-down time (minutes) KT10 | KT50 | KT90 | % Knock-down 8 h | % mortality 24 h |
|---|---|---|---|---|---|---|
| Example 3 | 0 | 16 | 20 | 26 | 100 | 100 |
| 5 mg/unit | 2 | 5 | 8 | 11 | 100 | 100 |
|  | 4 | 5 | 8 | 12 | 100 | 100 |
| Example 7 | 0 | n.a. | n.a. | n.a. | 5 | 79 |
| 5 mg/unit | 2 | n.a. | n.a. | n.a. | 0 | 79 |
|  | 4 | n.a. | n.a. | n.a. | 0 | 65 |
| Example 8 | 0 | 22 | 31 | 40 | 100 | 100 |
| 5 mg/unit | 2 | 12 | 29 | 41 | 100 | 100 |
|  | 4 | 18 | 32 | 50 | 100 | 100 |
| Transfluthrin | 0 | 21 | 26 | 35 | 100 | 100 |
| 5 mg/unit | 2 | 7 | 9 | 12 | 100 | 100 |
|  | 4 | 6 | 9 | 14 | 100 | 100 |
| Metofluthrin | 0 | 16 | 25 | 34 | 100 | 100 |
| 5 mg/unit | 2 | 7 | 9 | 15 | 100 | 100 |
|  | 4 | 6 | 8 | 14 | 100 | 100 |

TABLE 2

Tested species: *Culex quinquefasciatus*

| Compound | Insect exposure after the following hours | Knock-down time (minutes) KT10 | KT50 | KT90 | % Knock-down 8 h | % mortality 24 h |
|---|---|---|---|---|---|---|
| Example 3 | 0 | 23 | 28 | 35 | 100 | 100 |
| 5 mg/unit | 2 | 7 | 11 | 15 | 100 | 100 |
|  | 4 | 8 | 10 | 14 | 100 | 100 |
| Example 7 | 0 | n.a. | n.a. | n.a. | 8 | 70 |
| 5 mg/unit | 2 | n.a | n.a. | n.a. | 2 | 35 |
|  | 4 | n.a | n.a. | n.a. | 0 | 23 |
| Example 8 | 0 | 35 | 44 | 70 | 100 | 83 |
| 5 mg/unit | 2 | 39 | 50 | 68 | 100 | 70 |
|  | 4 | 39 | 53 | 66 | 100 | 61 |
| Transfluthrin | 0 | 31 | 42 | 55 | 100 | 100 |
| 5 mg/unit | 2 | 16 | 25 | 34 | 100 | 100 |
|  | 4 | 11 | 16 | 24 | 100 | 100 |
| Metofluthrin | 0 | 22 | 32 | 36 | 100 | 100 |
| 5 mg/unit | 2 | 11 | 16 | 22 | 100 | 100 |
|  | 4 | 10 | 14 | 20 | 100 | 100 |

The invention claimed is:

1. A compound of formula (I):

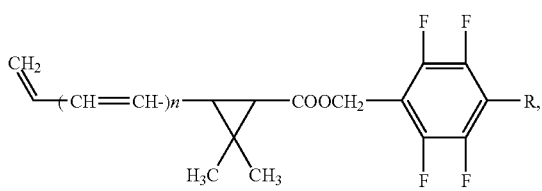

(I)

in which n is chosen from 1 and 2 and R is chosen from —H, —CH₃, C₂H₅, —OCH₃, —OC₂H₅, and CH₂—OCH₃, their enantiomers and diastereoisomers and mixtures thereof.

2. The compound according to claim 1, selected from the group consisting of:
2,3,5,6-tetrafluorobenzyl-(1RS,3RS)-3-((E/Z)-Buta-1,3-dienyl)-2,2-dimethylcyclopropane-1-carboxylate;
2,3,5,6-tetrafluorobenzyl-(1R,3R)-3-((E)-Buta-1,3-dienyl)-2,2-dimethylcyclopropane-1-carboxylate;
2,3,5,6-tetrafluorobenzyl-(1R,3R)-3-((E/Z)-Buta-1,3-dienyl)-2,2-dimethylcyclopropane-1-carboxylate;
2,3,5,6-tetrafluorobenzyl-(1R,3R)-3-(Hexa-1,3(E)-5(E/Z)-1,3,5-trienyl)-2,2-dimethylcyclopropane-1-carboxylate; and
2,3,5,6-tetrafluoro-4-methoxymethyl benzyl(1R,3R)-3-((E/Z)-Buta-1,3-dienyl)-2,2-dimethylcyclopropane-1 carboxylate.

3. A method for the elimination of insects from a substrate comprising the step of bringing said substrate into contact with an effective amount of one or more compounds of formula (I) as defined in claim 1.

4. The method according to claim 3 wherein said substrate is a domestic environment or a surface thereof, public premises or a surface thereof, a park, a garden, an agricultural surface.

5. A method for veterinary treatment with insecticidal activity comprising the step of administering to a subject in need thereof one or more compounds of formula (I) as defined in claim 1.

6. An insecticidal composition comprising one or more compounds of formula (I) as defined in claim 1 in combination with an excipient.

7. The composition according to claim 6 comprising a w/w percentage of compound (I) in the range from 0.001 to 95%.

8. The composition according to claim 6 comprising a w/w percentage of compound (I) in the range from 0.001 to 50%.

9. The composition according to claim 6 comprising a w/w percentage of compound (I) in the range from 0.001 to 5%.

10. A process for the synthesis of compounds of formula (I):

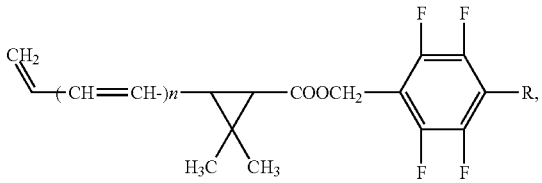

(I)

in which n is chosen from 1 and 2 and R is chosen from —H, —CH₃, C₂H₅, —OCH₃—OC₂H₅, and —CH₂—OCH₃ their enantiomers and diastereoisomers and mixtures thereof, comprising reacting a compound of formula (II):

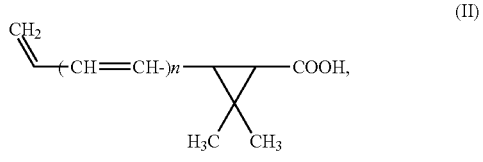

(II)

optionally activated at the —COOH group, with an alcohol of formula (III):

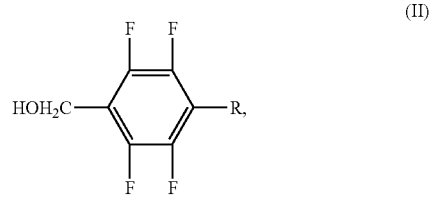

(II)

where n and R have the meanings described for formula (I).

11. The process according to claim 10 where the —COOH group is activated by formation of the corresponding acyl halide.

12. A process for the synthesis of compounds of formula (I):

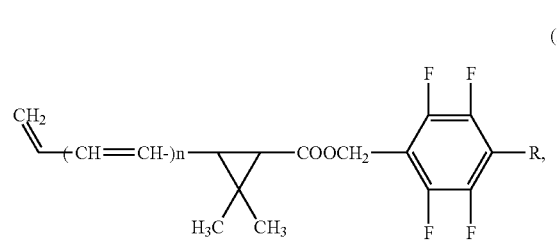

in which n is 2 and R is chosen from —H, —CH$_3$, C$_2$H$_5$, —OCH$_3$, —OC$_2$H$_5$, and —CH$_2$—OCH$_3$, their enantiomers and diastereoisomers and mixtures thereof, comprising the treatment of a compound of formula (VII):

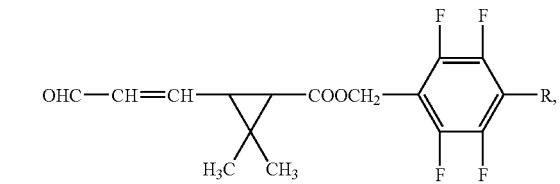

with an allyltriphenylphosphonium halide.

* * * * *